United States Patent [19]

Regelman

[11] Patent Number: 4,602,049

[45] Date of Patent: Jul. 22, 1986

[54] NOVEL PRODUCT AND PROCESS OF ISOCYANURATE PRODUCTION

[75] Inventor: Dale F. Regelman, Wallingford, Conn.

[73] Assignee: The Dow Chemical Company, Midland, Mich.

[21] Appl. No.: 778,647

[22] Filed: Sep. 23, 1985

Related U.S. Application Data

[62] Division of Ser. No. 571,391, Jan. 16, 1984, Pat. No. 4,567,257.

[51] Int. Cl.$^4$ ............................................. C08G 18/14
[52] U.S. Cl. ...................... 521/129; 502/164; 502/167; 528/53; 544/193; 544/193.1; 544/193.2
[58] Field of Search ............ 521/129; 528/53; 502/164, 167; 544/193, 193.1, 193.2

[56] References Cited

PUBLICATIONS

Advances in Organic Chemistry Methods and Results, 9, Iminium Salts in Organic Chemistry Part 2, pp. 321 et seq., 1979, John Wiley & Sons, N.Y.
The Organic Chemistry of Nitrogen by N. V. Sidgwick, 1942, p. 156, Oxford University Press, New York.
Taylor et al., J. Am. Chem. Soc., 82, 3138–3141, 1960.
Taylor et al, J. Org. Chem., 28, 1108 (1963).
D. H. Clemens et al., J. Org. Chem., 29, 2932 to 2936, 1964.

Primary Examiner—Maurice J. Welsh
Attorney, Agent, or Firm—James S. Rose

[57] ABSTRACT

Disclosed is a novel class of amidinium salts having the formula

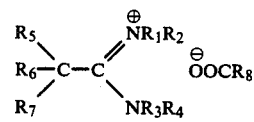

wherein $R_1$, $R_2$, $R_3$, and $R_4$ when taken individually are independently selected from lower-alkyl, aralkyl and cycloalkyl, and, when taken together with the respective nitrogen atoms to which they are attached, $R_1$ together with $R_2$, and $R_3$ together with $R_4$ independently represent heterocyclic groups having 5 to 7 ring atoms, $R_5$, $R_6$, $R_7$, and $R_8$ are independently selected from hydrogen, lower-alkyl, aryl, aralkyl, and cycloalkyl.

The amidinium salts are very active catalysts for converting organic isocyanates to products containing isocyanurate and carbodiimide linkages.

5 Claims, No Drawings

NOVEL PRODUCT AND PROCESS OF ISOCYANURATE PRODUCTION

This is a divisional, of application Ser. No. 571,391, filed Jan. 16, 1984 and now U.S. Pat. No. 4,567,257.

BACKGROUND OF THE INVENTION

1. Field of the Invention

This invention relates to novel amidinium compounds and is more particularly concerned with amidinium carboxylate salts and their use as catalysts in the polymerization of organic isocyanates.

2. Description of the Prior Art

Amidines in general are strongly basic compounds which are known to react with acids to form amidinium salts such as chlorides, sulfates, acetates, and the like. For a comprehensive review of amidinium salts and their chemistry see "Advances in Organic Chemistry Methods and Results" Vol. 9 Iminium Salts in Organic Chemistry Part 2, p 321 et seq, 1979, John Wiley and Sons, New York, N.Y.

The reported amidinium carboxylate salts are those of the simple unsubstituted amidines as generally disclosed in "The Organic Chemistry of Nitrogen" by N. V. Sidgwick revised by Taylor et al, p 156, 1942, Oxford University Press, New York, N.Y. and typically, acetamidine acetate (see Taylor et al, J. Am. Chem. Soc. 82, 3138–3141 [1960]). Also, certain N,N'-disubstituted formamidinium and acetamidinium acetates have been reported by Taylor et al, J. Org. Chem. 28, 1108 (1963).

The N,N,N',N'-tetrasubstituted amidinium salts which have been reported to date have included particular halide, perchlorate, picrate, hexafluorophosphate derivatives but not carboxylates; see "Advances in Organic Chemistry" Part 2 cited supra and D. H. Clemens et al, J. Org. Chem. 29, 2932–2936, 1964.

I have now discovered what I believe to be a novel class of N,N,N',N'-tetrasubstituted amidinium carboxylate salts which find particular utility in catalyzing the polymerization of organic polyisocyanates.

SUMMARY OF THE INVENTION

This invention comprises amidinium salts having the formula $$\begin{array}{c} R_5 \\ R_6-C-C \\ R_7 \end{array} \begin{array}{c} \overset{\oplus}{N}R_1R_2 \\ NR_3R_4 \end{array} \quad \overset{\ominus}{O}OCR_8 \quad (I)$$

wherein $R_1$, $R_2$, $R_3$, and $R_4$, when taken individually, are independently selected from the group consisting of loweralkyl, aralkyl and cycloalkyl, and, when taken together with the respective nitrogen atoms to which they are attached, $R_1$ together with $R_2$, and $R_3$ together with $R_4$ independently represent heterocyclic groups having 5 to 7 ring atoms; and $R_5$, $R_6$, $R_7$, and $R_8$ are independently selected from the group consisting of hydrogen, loweralkyl, aryl, aralkyl, and cycloalkyl.

The formula (I) is also meant to include any of the tautomeric resonance forms which can be drawn from the formula (I) wherein the double bond is connected to the other nitrogen atom or any resonance hybrid intermediate between the two structures.

This invention also comprises a method for converting organic isocyanates into products containing isocyanurate and carbodiimide linkages by contacting said isocyanates with a catalyst comprising an amidinium salt (I) as defined above.

This invention also comprises the products prepared by the method set forth above.

The term "lower-alkyl" means alkyl having from 1 to 8 carbon atoms, inclusive, such as methyl, ethyl, propyl, butyl, pentyl, hexyl, heptyl, octyl, and isomeric forms thereof.

The term "aralkyl" means the monovalent radical obtained by removing one hydrogen atom from the alkyl portion of an aromatic alkane hydrocarbon having 7 to 18 carbon atoms. Illustrative of aralkyl are benzyl, phenethyl, phenylpropyl, benzhydryl, naphthylmethyl, and the like.

The term "cycloalkyl" means cycloalkyl having 4 to 6 ring carbon atoms, inclusive, such as cyclobutyl, cyclopentyl, cyclohexyl, 3-methylcyclopentyl, 4-methylcyclohexyl, and the like.

The term "heterocyclic groups having 5 to 7 ring atoms" means heterocyclic radicals containing at least the basic valence ring nitrogen and optionally containing one or more additional hetero atoms such as nitrogen, oxygen, and sulfur. Illustrative of such groups are N-pyrrolidinyl, N-oxazolidinyl, N-thiazolidinyl, N-piperidinyl, N-(4-methylpiperidinyl), N-morpholinyl, N-(4-methylpiperazinyl), N-(4-ethylpiperazinyl), N-hexahydroazepinyl, and the like.

The term "aryl" means the radical obtained by removing one nuclear hydrogen atom from an aromatic hydrocarbon having from 6 to 12 carbon atoms, inclusive. Illustrative of aryl are phenyl, tolyl, naphthyl, biphenylyl, and the like.

DETAILED DESCRIPTION OF THE INVENTION

The novel amidinium salts in accordance with the present invention are defined by the formula (I) set forth above.

Illustrative but not limiting of the amidinium salts are the following

1. Acetamidinium Salts:

N,N,N',N'-tetramethylacetamidinium, N,N,N',N'-tetraethylacetamidinium, N,N,N',N'-tetrabutylacetamidinium, N,N,N',N'-tetrahexylacetamidinium, N,N,N',N'-tetraoctylacetamidinium, N,N,N',N'-tetracyclopentylacetamidinium, N,N,N',N'-tetracyclohexylacetamidinium, N,N,N',N'-tetrabenzylacetamidinium, N,N-dimethyl-N',N'-diethylacetamidinium, N,N'-dimethyl-N,N'-diethylacetamidinium, N,N'-dimethyl-N,N'-dibenzylacetamidinium, N,N'-dimethyl-N,N'-dicyclohexylacetamidinium, N,N'-bis(tetramethylene)acetamidinium (one pyrrolidinyl and one pyrrolidinium ring), N,N'-bis(2-oxatetramethylene)acetamidinium (one oxazolidinyl and one oxazolidinium ring), N,N'-bis(2-thiatetramethylene)acetamidinium (one thiazolidinyl and one thiazolidinium ring), N,N'-bis(pentamethylene)acetamidinium (one piperidinyl and one piperidinium ring), N,N'-bis(3-oxapentamethylene)acetamidinium (one morpholinyl and one morpholinium ring), N,N'-bis(tetramethylene)phenylacetamidinium, N,N'-bis(tetramethylene) cyclopentylacetamidinium, and N,N'-bis(tetramethylene) cyclohexylacetamidinium formates, acetates, propionates, butyrates, 2-ethylhexanoates, phenylacetates, benzoates, and cyclohexane carboxylates.

2. Propionamidinium Salts:

N,N,N',N'-tetramethylpropionamidinium, N,N,N',N'-tetraethylpropionamidinium, N,N,N',N'-tetrabutylpropionamidinium, N,N,N',N'-tetrabenzylpropionamidinium, N,N'-bis(tetramethylene)propionamidinium, N,N'-bis(2-oxatetramethylene)propionamidinium, N,N'-bis(2-thiatetramethylene)propionamidinium, N,N'-bis(pentamethylene) propionamidinium, and N,N'-bis(3-oxapentamethylene) propionamidinium formates, acetates, propionates, butyrates, 2-ethylhexanoates, phenylacetates, benzoates, and cyclohexane carboxylates.

3. Butyramidinium Salts:

N,N,N',N'-tetramethylbutyramidinium, N,N,N',N'-tetraethylbutyramidinium, N,N,N',N'-tetrabutylbutyramidinium, N,N,N',N'-tetrabenzylbutyramidinium, N,N'-bis(tetramethylene)butyramidinium, N,N'-bis(2-oxatetramethylene)butyramidinium, N,N'-bis(2-thiatetramethylene)butyramidinium, N,N'-bis(pentamethylene)butyramidinium, and N,N'-bis(3-oxapentamethylene)butyramidinium formates, acetates, propionates, butyrates, 2-ethylhexanoates, phenylacetates, benzoates, and cyclohexane carboxylates.

4. Pentanamidinium Salts:

N,N,N',N'-tetramethylpentanamidinium, N,N,N',N'-tetraethylpentanamidinium, N,N,N',N'-tetrabutylpentanamidinium, N,N,N',N'-tetrabenzylpentanamidinium, N,N'-bis(tetramethylene)pentanamidinium, N,N'-bis(2-oxatetramethylene) pentanamidinium, N,N'-bis(2-thiatetramethylene)pentanamidinium, N,N'-bis(pentamethylene)pentanamidinium, and N,N'-bis(3-oxapentamethylene)pentanamidinium formates, acetates, propionates, butyrates, 2-ethylhexanoates, phenylacetates, benzoates, and cyclohexane carboxylates.

5. Hexanamidinium Salts:

N,N,N',N'-tetramethylhexanamidinium, N,N,N',N'-tetraethylhexanamidinium, N,N,N',N'-tetrabutylhexanamidinium, N,N,N',N'-tetrabenzylhexanamidinium, N,N'-bis(tetramethylene)hexanamidinium, N,N'-bis(2-oxatetramethylene) hexanamidinium, N,N'-bis(2-thiatetramethylene)hexanamidinium, N,N'-bis(pentamethylene)hexanamidinium, and N,N'-bis(3-oxapentamethylene)hexanamidinium formates, acetates, propionates, butyrates, 2-ethylhexanoates, phenylacetates, benzoates, and cyclohexane carboxylates.

6. Higher Amidinium Salts:

N,N'-bis(tetramethylene)heptanamidinium, N,N'-bis(pentamethylene)heptanamidinium, N,N'-bis(3-oxapentamethylene) heptanamidinium, N,N'-bis(tetramethylene)octanamidinium, N,N'-bis(pentamethylene)octanamidinium, N,N'-bis(3-oxapentamethylene)octanamidinium, N,N'-bis(tetramethylene) nonanamidinium, N,N'-bis(pentamethylene)nonanamidinium, N,N'-bis(3-oxapentamethylene)nonanamidinium, N,N'-bis (tetramethylene)decanamidinium, N,N'-bis(pentamethylene)decanamidinium, and N,N'-bis(3-oxapentamethylene)decanamidinium formates, acetates, propionates, butyrates, 2-ethylhexanoates, phenylacetates, benzoates, and cyclohexane carboxylates.

The amidinium compounds of formula (I) can be prepared by processes which are analogous to those known in the art. Illustratively, when it is desired to make those compounds in which at least one of the $R_5$, $R_6$, or $R_7$ substituents is hydrogen, the salts of the invention are easily prepared using the methods described by Clemens et al [J. Org. Chem. 29, 2932 et seq. (1964)] wherein a ketene aminal (II) is reacted with a carboxylic acid (III) in a simple acid-base neutralization reaction according to the following equation

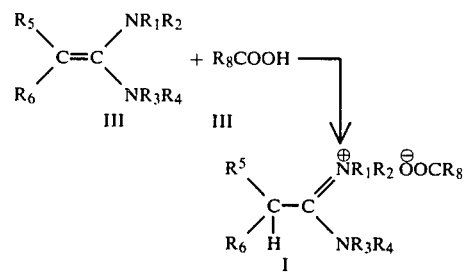

wherein $R_1$, $R_2$, $R_3$, $R_4$, $R_5$, $R_6$, and $R_8$ are defined above.

Alternatively, and as another means for varying any one of the $R_5$, $R_6$, or $R_7$ substituents, the ketene-aminals (II) can be arylated, cycloalkylated, or alkylated to the corresponding halide salt (V) using the method described by Clemens et al cited supra. The halide salt (V) in turn is easily converted to an amidinium compound (I) in accordance with the present invention simply by the well known acid displacement reaction. This alternative preparation is set forth in the following reaction scheme

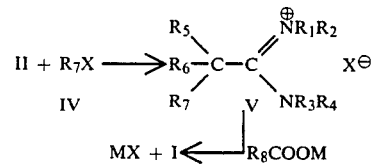

wherein $R_1$, $R_2$, $R_3$, $R_4$, $R_5$, $R_6$, and $R_8$ are as defined above, IV is a typical alkyl halide wherein X represents halogen (i.e. fluorine, chlorine, bromine, and iodine), and M is illustratively an alkali metal ion such as sodium, potassium, and lithium.

The preparation of the amidinium salts is advantageously carried out by mixing the above ingredients in the presence of an inert organic solvent. By "inert organic solvent" is meant an organic solvent which does not enter into reaction with any of the above reactants or otherwise interfere in any manner with the desired course of the reaction. Illustrative of inert organic solvents are polar aromatic solvents such as nitrobenzene, dichlorobenzene, toluene, xylene, and the like; halogenated aliphatic solvents such as chloroform, carbon tetrachloride, tetrachloroethane, and the like; dipolar aprotic solvents such as acetonitrile, formamide, dimethylformamide, diethylformamide, dimethylacetamide, dimethylsulfoxide, tetramethylenesulfone, hexamethylphosphoramide, tetramethylurea, and the like; alcohols such as methanol, ethanol, isopropanol, cyclohexanol, and the like; organic polyols having at least two hydroxyl groups and inclusive of organic polyols having a M.W. of from about 60 to about 4000, such as ethylene glycol, diethylene glycol, propylene glycol, dipropylene glycol, liquid polyethyleneoxy glycols, liquid polyethyleneoxypolypropyleneoxy glycols, and the like.

The reaction of (II) with (III) carried out in any of the above solvents is essentially instantaneous upon mixing at ambient (20° C.) temperature and is exothermic but can be effected over a wide range of temperatures, illustratively from −10° C. to about 80° C. and, preferably, from about 0° C. to about 25° C. In the event that (II) is reacted with an alkyl halide (IV) as described above this reaction too, generally speaking, is exothermic and can be subjected to the same preparative temperature range set forth for the simple neutralization method. The progress of either reaction can be monitored by conventional analytical procedures such as by infrared spectroscopy, nuclear magnetic resonance spectroscopy and like analytical methods. When the product is the intermediate salt (V), the halide ion is simply displaced by $R_8COO^\ominus$ by the addition of an appropriate salt $R_8COOM$ where $R_8$ and M have the significance defined above.

The products are easily isolated using conventional isolation techniques. Illustratively, the reaction solvent is removed by simple distillation either at atmospheric or reduced pressure to provide the product. In the event that the alternative preparation is employed [i.e. the reaction of the aminal (II) and the alkyl halide (IV)] the precipitated MX salt is filtered off prior to solvent removal. The product so obtained can be purefied by routine procedures such as recrystallization when the product is a solid or by reprecipitation, chromatography and the like in the case of a liquid product.

In an alternative, and, preferred, embodiment of the invention the amidinium salts are prepared as a solution in an organic polyol and left therein to be used as isocyanate polymerization catalysts. The concentration of the salt in the polyol is in no way critical and is advantageously from about 10 to about 75 percent, preferably 20 to 50 percent, by weight based on the weight of salt and polyol.

The ketene-aminal starting compounds are all well known materials in the prior art and are typically prepared by reacting an excess of the appropriate secondary amine(s) with the appropriate acetal or ethoxyacetylene according to the procedures set forth or referenced in Clemens et al cited supra.

The amidinium salts (I) in accordance with the present invention have been found to be very active catalysts for converting organic isocyanates into products containing both isocyanurate and carbodiimide linkages. Generally speaking, the prior art teaches that more than one catalyst is required whenever it is desired to convert an isocyanate into an isocyanurate-carbodiimide product; for example see U.S. Pat. Nos. 3,657,161 and 3,887,501.

Further, certain of the amidinium salts (I) give rise to extremely fast polymerization profiles, for example, in some cases in a matter of seconds. This feature is highly unexpected in the formation of isocyanurate-carbodiimide linkages and becomes very useful when cellular polymers are being prepared.

The salts having the formula (I) behave quite differently from the corresponding amidinium inorganic salts such as sulfates and perchlorates which latter salts are devoid of any activity in respect of polymerizing an organic isocyanate (see Example 7 below).

The amidinium compounds in accordance with the present invention can be used as catalysts for the preparation of a broad variety of products arising from the polymerization of isocyanates including solid polymers such as solid and micro-cellular elastomers, RIM elastomers, and the like; isocyanurate-carbodiimide containing polyisocyanate prepolymers; and cellular polymers when reacted under foam forming conditions.

Typical procedures and ingredients which can be used in combination with the amidinium salt catalysts for the preparation of polyisocyanurate-polycarbodiimide solids, foams, and prepolymers are set forth in U.S. Pat. Nos. 3,711,444; 3,896,052; 3,903,018 and 4,111,914 whose disclosures relative thereto are hereby incorporated herein by reference.

Advantageously, the amidinium salt (I) catalyst is employed in an amount falling within a range of from about 0.05 to about 10 mole percent, preferably from about 0.1 to about 5 mole percent per mole of isocyanate being polymerized.

As noted previously, the amidinium salt is preferably employed in the polymerization process as a solution in a polyol as defined above.

While any of the amidinium salts (I) of the invention can be employed as catalysts in the manner described above, preferred are those salts wherein $R_1$, $R_2$, $R_3$, and $R_4$ represent the same group, which, in the case of the heterocyclic groups that both are the same, $R_5$ and $R_6$ are both hydrogen, and $R_7$ and $R_8$ are both lower-alkyl. Most preferred as a class are the amidinium salts wherein $R_1$, $R_2$, $R_3$, and $R_4$ represent the same heterocyclic groups defined above, $R_5$ and $R_6$ are hydrogen, and $R_7$ and $R_8$ both represent $C_1$ to $C_4$ alkyl.

Preferred species of the amidinium salts are the acetates, propionates, and butyrates of the propionamidinium, butyramidinium, pentanamidinium, and hexanamidinium compounds set forth above having the same heterocyclic groups. Most preferred are the acetate salts thereof.

The isocyanates which can be polymerized in accordance with the present invention can be any of the organic isocyanates, particularly organic polyisocyanates known to those skilled in the art which are referred to in the patents cited supra.

Typical, but not limiting, of the isocyanates which can be used are phenyl isocyanate, hexamethylene diisocyanate, 4,4'-methylenebis(phenyl isocyanate), m- and p-phenylene diisocyanate, 2,4- and 2,6-toluene diisocyanate and mixtures of the 2,4- and 2,6-isomers, polymethylenepolyphenyl polyisocyanates, the various types of liquefied methylenebis(phenyl isocyanates) obtained by reacting the methylenebis(phenyl isocyanate) in varying proportions with minor amounts of one or more glycols and the liquid diisocyanates comprising the carbodiimide-containing methylenebis(phenyl isocyanates) having an isocyanate equivalent weight of from about 130 to about 180. Also included within the scope of the present invention are isocyanate terminated polyurethane prepolymers.

Preferred amongst the typical species cited above are the aromatic polyisocyanates and hexamethylene diisocyanate.

The various products described above which are derived by the isocyanate polymerization methods in accordance with the present invention can be used in a variety of applications. For instance, solid molded parts derived from these polymers are useful in the production of auto parts such as body elements, panels, doors, engine hoods, and the like. Cellular products derived from these polymers, by virtue of their high temperature resistance qualities, can be used as thermal barriers and insulation materials for high temperature pipe lines, ovens, storage tanks, and in the production of flame retardant laminates.

The following examples describe the manner and process of making and using the invention and set forth the best mode contemplated by the inventor of carrying out the invention but are not to be construed as limiting.

EXAMPLE 1

Preparation of
N,N'-Bis(pentamethylene)propionamidinium acetate

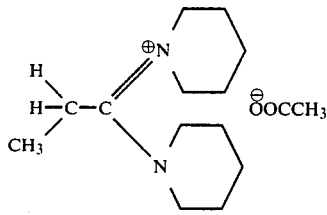

A small (2 oz.) wide-mouth sample bottle equipped with a magnetic stirring bar was charged with 0.53 g. (0.0087 mole) of acetic acid dissolved in 5 g. of deuterated chloroform. During stirring a 1.82 g. (0.0087 mole) sample of 1,1-bis(N-piperidinyl)-2-methylethylene was added dropwise to the acetic acid solution which caused the solution to exotherm to about 58° C.

Thus there was obtained N,N'-bis(pentamethylene) propionamidinium acetate in accordance with the present invention as a 32 percent by weight solution in the deuterated chloroform. Infrared analysis showed the absence of free acetic acid and strong stretching for the carboxylate anion. Proton nuclear magnetic resonance (NMR) substantiated the presence of amidinium cation in good agreement with the NMR data of Clemens et al cited supra.

The above experiment was repeated using the same procedure and ingredients except that the deuterated chloroform was replaced by non-deuterated chloroform. At the conclusion of the reaction the chloroform was removed by distillation under a strong argon purge. The N,N'-bis(pentamethylene)propionamidinium acetate was obtained as a brown liquid. Upon storage in a vacuum desiccator under about 0.1 mm mercury pressure for 3 days the product did not crystallize. It remained as a brown liquid after attempts to recrystallize it from both pentane and cyclohexane failed.

EXAMPLE 2

Preparation of
N,N'-Bis(3-oxapentamethylene)propionamidinium acetate

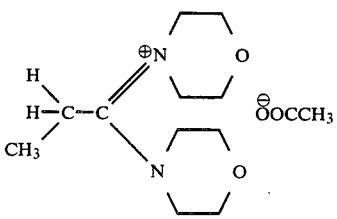

Using the same apparatus and procedure set forth in Example 1 except for reverse addition, 3.60 g. (0.017 mole) of 1,1-bis(N-morpholinyl)-2-methylethylene was dissolved in 10 g. of Poly G 55-112 (a 1000 MW polyoxyethylene-polyoxypropylene diol having an EO content of about 50 percent by weight and supplied by Olin Chemicals, New Haven, Conn.). To the stirred solution at about 20° C. was added dropwise 1.049 g. (0.017 mole) of acetic acid causing the solution to exotherm to about 43° C.

Thus there was obtained N,N'-bis(3-oxapentamethylene) propionamidinium acetate in accordance with the present invention as a 32 percent by weight solution in the Poly G 55-112.

The preparation of N,N'-bis(3-oxapentamethylene) propionamidinium acetate was repeated using the same procedure described above except that reactant quantities were reduced to 1.84 g. of the 1,1-bis(N-morpholinyl)-2-methylethylene and 0.53 g. of acetic acid (0.0087 mole each) and the solvent was 5.0 ml. of chloroform. At the conclusion of the reaction the solvent was removed by distillation under a strong argon purge. The product was obtained as a brown oil which formed a brown pasty solid after storage for 3 days under about 0.1 mm of mercury pressure in a vacuum desiccator.

EXAMPLE 3

Preparation of
N,N'-Bis(tetramethylene)propionamidinium acetate

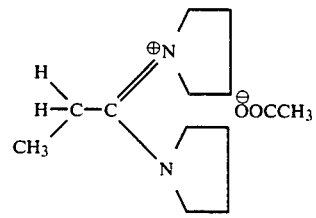

Using the same apparatus and procedure set forth in Example 1, 1.049 g. (0.017 mole) of acetic acid was dissolved in 10 g. of Poly G 55-112. During stirring at about 20° C. a 5 g. sample consisting of 60 percent by weight (0.017 mole) of 1,1-bis(N-pyrrolidinyl)-2-methylethylene and the remaining 40 percent N-propionylpyrrolidine as an impurity was added to the acetic acid solution causing an exotherm to about 47° C. The N-propionylpyrrolidine was formed as a by-product during the preparation of the 1,1-bis(N-pyrrolidinyl)-2-methylethylene by the reaction of pyrrolidine with ethyl orthopropionate.

Thus there was obtained N,N'-bis(tetramethylene) propionamidinium acetate in accordance with the present invention as a 29 percent by weight solution (4.05 g. of product) in Poly G 55-112 and which solution also contained as an impurity the N-propionylpyrrolidine noted above.

EXAMPLE 4

The following example describes two polymerization reactions of a liquefied methylenebis(phenyl isocyanate) containing about 0.056 equivalent of carbodiimide (I.E. = 144) to form solid polyisocyanurate-polycarbodiimide products in accordance with the present invention.

Two separate wide-mouth glass jars were each charged with 100 g. of the above described liquefied methylenebis(phenyl isocyanate). Into one jar 2.35 g. of N,N'-bis(pentamethylene)propionamidinium acetate dissolved in 5 ml. of deuterated chloroform [prepared in accordance with Example 1 above] was thoroughly blended with the isocyanate using a spatula. An immediate evolution of gas was noted by the formation of bubbles which were easily stirred out of the liquid isocyanate. A slow exotherm ensued which reached a maximum of 45° C. over a 30 minute period. After about 45 minutes a solid brittle polymer was obtained. Infrared analysis showed a mixture of polycarbodiimide and polyisocyanurate linkages with a predominance of the latter.

Into the second 100 g. sample of liquefied isocyanate at about 23° C. there was added 4.65 g. of N,N'-bis(3-oxapentamethylene)propionamidinium acetate dissolved in 10 g. of Poly G 55-112 (prepared in accordance with the method set forth in Example 2 above) and the mixture was thoroughly blended with a spatula. There was an immediate and heavy evolution of carbon dioxide and a rapid rise in temperature to about 37° C. The reaction mixture cooled slowly (over about 45 minutes) to ambient room temperature yielding a solid polymer. Infrared analysis showed a mixture of polycarbodiimide and polyisocyanurate linkages with a predominance of the latter.

EXAMPLE 5

The following example describes the preparation of two isocyanate terminated prepolymers containing carbodiimide and isocyanurate moieties in accordance with the present invention. One was an aromatic polyisocyanate prepolymer and the other was based on an aliphatic polyisocyanate.

Using the same procedure described in Example 4, to a glass jar containing 200 g. of molten 4,4'-methylenebis(phenyl isocyanate) (MDI) which was obtained by warming the solid MDI to about 42° C. there was added 4.65 g. of N,N'-bis(3-oxapentamethylene)propionamidinium acetate dissolved in 10 g. of Poly G 55-112 (prepared in accordance with the method set forth in Example 2 above). The mixture was thoroughly blended with a spatula and the temperature rose to 53° C. The mixture was allowed to cool and after standing overnight a yellow pasty product was obtained; I.E.=198; infrared showed the presence of trimer, carbodiimide and a lesser proportion of dimer linkages.

In a second jar 100 ml. of hexamethylene diisocyanate at 22° C. was mixed with 4.05 g. of N,N'-bis(tetramethylene) propionamidinium acetate dissolved in 10 g. of Poly G 55-112 (prepared in accordance with the method set forth in Example 3 and also containing the N-propionylpyrrolidine impurity). A maximum exotherm of 45° C. was reached after about 10 minutes. The reaction cooled slowly over about 2 hours to 22° C. yielding an orange, slightly viscous product; I.E.=84.

EXAMPLE 6

The following example describes the preparation of two polyisocyanurate-polycarbodiimide cellular polymers both in accordance with the present invention.

In the first experiment, 200 ml. of the liquefied MDI described in Example 4 was placed in a paper cup and to the isocyanate there was added 4.05 g. of N,N'-bis(tetramethylene)propionamidinium acetate dissolved in 10 g. of Poly G 55-112 (prepared in accordance with the method set forth in Example 3 and also containing the N-propionylpyrrolidine impurity). The mixture was stirred vigorously using a metal stirring blade connected to a drill press motor. An immediate foaming reaction (in about 2 seconds) occurred which resulted in the formation of a solid cellular polymer having about 10 times the volume of the original isocyanate. A peak exotherm inside the foam was measured at 160° C. After cooling to room temperature (20° C.), the foam (with no postcure) exhibited good skin and high compressive strength determined by manually pressing it. Infrared analysis showed the presence of isocyanurate and carbodiimide linkages.

The second cellular polymer was prepared using the same procedure, proportions, and reactants set forth above except that the isocyanate employed was a polymethylene polyphenyl isocyanate mixture comprising about 62 percent of methylenebis(phenyl isocyanate) wherein the ortho-para content was about 12 percent and the para-para content 88 percent, and the remainder of the mixture comprising polymethylene polyphenyl isocyanates having functionalities greater than 2.0; I.E.=132. The foaming reaction occurred immediately which resulted in a cellular polymer about 10 times the original isocyanate volume in about 2 seconds. Infrared analysis showed the presence of isocyanurate and carbodiimide linkages.

EXAMPLE 7

The following example sets forth a comparison of the catalytic activity (for isocyanate polymerization) of four different compounds. Two of the compounds were amidinium salts not within the scope of the present invention, the third compound was an amidinium salt in accordance with the present invention while the fourth compound was the starting ketene-aminal from which the three amidinium salts were prepared.

The starting material for each amidinium salt was 1.53 g. of the ketene-aminal of 1,1-bis(N-pyrrolidinyl)-2-methylethylene dissolved in 5.0 g. of Poly G 55-112. The two amidinium salts not in accordance with the present invention were the sulfate and perchlorate salts prepared from this ketene-aminal in accordance with Clemens et al cited supra by reaction with the appropriate amount of sulfuric and perchloric acids and the third salt was the acetate prepared according to Example 3 above using the appropriate amount of acetic acid.

Four separate 100 g. samples of the liquefied MDI described in Example 4 were each mixed with the respective test compounds dissolved in the 5.0 g. of Poly G 55-112 using the method described in Example 6. In the case of the ketene-aminal a 1.53 g. sample dissolved in 5.0 g. of Poly G 55-112 was employed.

In the case of the amidinium sulfate and perchlorate no reaction of the isocyanate could be detected.

For the third compound, the amidinium acetate, a foamed polymer was formed almost instantly upon the catalyst addition. Infrared analysis confirmed the presence of isocyanurate and carbodiimide linkages and a lesser amount of dimer linkages.

In the case of the ketene-aminal, when it was vigorously stirred into the MDI it formed a small mass of material of higher viscosity than the surrounding liquefied and unreacted MDI. However, there was no evidence of gas formation (i.e. no carbodiimide formation) and after prolonged standing the MDI solidified slowly. The slow solidification was assumed to be occurring through trimerization of the isocyanate which was catalyzed by the tertiary nitrogens of the ketene-aminal via a known catalysis route, and, additionally, the reaction of the active proton of the ketene-aminal with the isocyanate via known reaction steps.

I claim:

1. A method for converting an organic isocyanate into a product containing isocyanurate and carbodiimide linkages said method comprising contacting said isocyanate with a catalyst comprising an amidinium salt having the formula

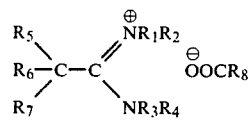

wherein $R_1$, $R_2$, $R_3$, and $R_4$, when taken individually, are independently selected from the group consisting of lower-alkyl, aralkyl, cycloalkyl, and, when taken together with the respective nitrogen atoms to which they are attached $R_1$ together with $R_2$ and $R_3$ together with $R_4$ independently represent heterocyclic groups have 5 to 7 ring atoms, and $R_5$, $R_6$, $R_7$, and $R_8$ are independently selected from the group consisting of hydrogen, lower-alkyl, aryl, aralkyl, and cycloalkyl.

2. A method according to claim 1 wherein an aromatic polyisocyanate is converted to a product containing isocyanurate and carbodiimide linkages.

3. A method according to claim 1 wherein an aliphatic polyisocyanate is converted to a polyisocyanate prepolymer containing isocyanurate and carbodiimide linkages.

4. A polyol solution of an amidinium salt having the formula

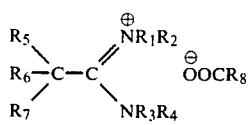

wherein, $R_1$, $R_2$, $R_3$, and $R_4$, when taken individually, are independently selected from the group consisting of lower-alkyl, aralkyl, cycloalkyl, and, when taken together with the respective nitrogen atoms to which they are attached $R_1$ together with $R_2$ and $R_3$ together with $R_4$ independently represent heterocyclic groups having 5 to 7 ring atoms, and $R_5$, $R_6$, $R_7$, and $R_8$ are independently selected from the group consisting of hydrogen, lower-alkyl, aryl, aralkyl, and cycloalkyl.

5. A method for the preparation of a cellular polymer characterized by isocyanurate and carbodiimide linkages said method comprising contacting under foam forming conditions an aromatic polyisocyanate with a catalyst comprising an amidinium salt in accordance with claim 4.

* * * * *